United States Patent [19]

Zambon et al.

[11] Patent Number: 4,994,376
[45] Date of Patent: Feb. 19, 1991

[54] DETECTION OF BACTEROIDES GINGIVALIS

[75] Inventors: Joseph J. Zambon, Williamsville; Robert J. Gence, Buffalo, both of N.Y.

[73] Assignee: The Research Foundation of State University of NY, Albany, N.Y.

[21] Appl. No.: 54,617

[22] Filed: May 27, 1987

[51] Int. Cl.$^5$ .......................... C12Q 1/37; C12Q 1/02; C12Q 1/04; C12N 9/99
[52] U.S. Cl. ........................................ 435/24; 435/29; 435/34; 435/184; 435/822; 530/300; 530/330; 530/825
[58] Field of Search ..................... 435/24, 29, 34, 184, 435/23, 13, 184, 822; 530/320, 330, 331, 825

[56] References Cited

U.S. PATENT DOCUMENTS 4,294,923 10/1981 Smith et al. ............................ 435/24
4,603,108  7/1986 Bascomb ................................ 435/24

FOREIGN PATENT DOCUMENTS 0074693 6/1976 Japan .................................... 435/24
1056100 3/1986 Japan .................................... 435/24
2079798 4/1987 Japan .................................... 435/24

OTHER PUBLICATIONS

Kamaev, M. F., *Klin. Med* (Moscow), 50 (7), pp. 13–16, 1972.
Worowski, Krzysztof, *Acta Pol. Pharm.*, 1979, 36(4), pp. 487–490.
Nakamura et al, *Dipeptidyl Arylamidase Activity of Bacteriodes Gingivalis,* 1984, Microbios Letters 25, pp. 157–160.
Suido et al, *Characterization of N–CBz–Glycyl–Glycyl–Arginyl Peptidase and Glycyl–Prelyl Peptidase of Bacteroides Gingivalis,* Journal of Periodontal Research 1987; 22: pp. 412–418.
Slots, *Journal of Clinical Microbiology*, Sep. 1981, "Enzymatic Characterization of Some Oral and Nonoral Gram Negative Bacteria with the API ZYM System", pp. 288–294.
Laughon et al, *Journal of Clinical Microbiology*, Jan. 1982, "API ZYM System for Identification of Bacteroides spp., Capnocytophaga spp., and Spirochetes of Oral Origin", pp. 97–104.
Yoshimura et al, *Archives of Oral Biology*, Nov. 7, 1984, "Characterization of a Trypsin–Like Protease from the Bacterium Bacteroides Gingivalis Isolated from Human Dental Plaque", pp. 559–564.
Abiko et al, *Journal of Dental Research*, Feb. 1985, "Glycylprolyl Dipeptidylaminopeptidase from Bacteroides Gingivalis", pp. 106–111.
Dellinger et al, *Journal of Clinical Microbiology*, Feb. 1986, "Use of the RapID–ANA System to Screen for Enzyme Activities That Differ Among Species of Bile–Inhibited Bacteroides", pp. 289–293.
Suido et al, *Journal of Dental Research*, Nov. 1987, "Arylaminopeptidase Activities of Oral Bacteria", pp. 1335–1340.

Primary Examiner—Esther L. Kepplinger
Assistant Examiner—Florina B. Hoffer
Attorney, Agent, or Firm—Michael L. Dunn; Ellen K. Park; Donald C. Studley

[57] ABSTRACT

The present invention relates to the detection of *B. gingivalis* by the specific ability of *B. gingivalis* to hydrolyze N-carbobenzoxy-glycyl-glycyl-L-arginine-B-napthylamide derivatives. The present invention also relates to the use of assay systems which inhibit serum amino peptidase and enhance the detection of the *B. gingivalis* N-CBz-Gly-Gly-Arg peptidase. The assay system inhibits the serum enzyme by the use of a serum aminopeptidase inhibitor which inhibits the activity of serum aminopeptidase to a greater extent that it inhibits the activity of *B. gingivalis* N-CBz-Gly-Gly-Arg peptidase. The assay system also increases the reliability of detection of the *B. gingivalis* enzyme by the use of enhancing materials which enhance the enzyme activity of *B. gingivalis* N-CBz-Gly-Gly-Arg peptidase to a greater extent than such materials enhance the enzyme activity of serum aminopeptidase.

5 Claims, 1 Drawing Sheet

DETECTION OF BACTEROIDES GINGIVALIS

This invention was made with government support under National Institute of Health—Periodontal Disease Clinical Research Center—Grant No. DE-04898.

BACKGROUND AND PRIOR ART

The present invention relates to the identification of *Bacteroides gingivalis* in biological samples by detection of a specific peptidase activity of *B. gingivalis*. The detection is suitably carried out by a colorimetric analysis of enzymes uniquely provided by *B. gingivalis*.

Certain species of gram negative bacteria, such as *B. gingivalis*, have been implicated in the etiology and pathogenesis of certain forms of periodontal disease. Such pathogenic bacteria secrete enzymes which are strongly suspect in pathogenesis of periodontal infections. For example, proteolytic enzymes such as collagenase, neuraminidase, fibrinolysin, trypsin like enzymes, and aminopeptidases are produced by various oral microorganisms and are closely associated with periodontal destruction.

Clinical assays specific to *B. gingivalis* in gingival and subgingival dental plaque are particularly useful in the diagnosis of periodontal disease, in evaluating the progress of periodontal therapy, and in determining the status of the patient at recall examinations. The standard bacteriological techniques presently in use to identify such microorganisms are time consuming, expensive, and require a high level of technical expertise. Further, such tests frequently give results which are not as accurate or as sensitive as may be desired or required.

Previously, studies have been carried out in attempts to identify *B. gingivalis* by its proteolytic activity. Much of this work has been done to specifically identify enzymes which are strongly associated with periodontal disease. However, many of the enzymes strongly associated with periodontal disease are not singularly specific to *B. gingivalis*. Examples of prior art studies are:

1. Yoshimura et al., *Archives of Oral Biology*, 1984, reports a trypsin-like membrane bound protease from *B. gingivalis* which hydrolyzes benzoyl-L-arginine-p-nitroanilide (L-BAPA), benzoyl-DL-arginine-β-napthylamide (BANA) and tosyl-L-arginine methyl ester. This enzyme activity is not specific to *B. gingivalis*. The same enzyme activity is found, for example, in *Treponema denticola*.

2. Abiko et al.; *Journal of Dental Research*, 1985, reports the purification an enzyme from *B. gingivalis* which degrades dipeptidyl substrates. This enzyme is not specific to *B. gingivalis*. It is also found in Capnocytophaga.

3. Dellinger and Moore, *Journal of Clinical Microbiology*, 1986, report the use of a commercially available system, RapID-ANA, for the identification of bacterial species. This system consists of a number of protein and sugar substrates and the bacteria are identified by their pattern of reactivity. *B. gingivalis* may be identified, but only through a series of separate eliminations steps.

4. Laughon et al., *Journal of Clinical Microbiology*, 1982, reports the use of a commercially available system, API-ZYM, for the identification of oral bacterial species. The substrates are protein or sugars. A common trypsin-like activity was found in *B. gingivalis*, *T. denticola*, and Capnocytophaga, however, the activity is not specific for *B. gingivalis*.

The present invention relates to the selective, singular detection of *B. gingivalis* by detection of a bacterial enzyme specific to *B. gingivalis*. Bacterial enzymes may be classified as either constitutive or adaptive. Constitutive enzymes are those enzymes which are formed by the bacterial cell wall under substantially all conditions of growth. In contrast, adaptive enzymes are those enzymes formed by the bacterial cell only in response to an inducer. Adaptive enzymes allow the cell to control to some extent the environment in which the cell lives. In nature the inducer is usually the substrate for the specific adaptive enzyme involved. Bacterial enzymes may also be divided into enzymes remaining in the cell (endoenzymes) and enzymes secreted by the cell into the surrounding medium (exoenzymes).

The enzymes utilized in the present invention are both adaptive and endoenzymes.

BRIEF DESCRIPTION OF THE INVENTION

The present invention relates to the detection of *B. gingivalis* by its specific ability to hydrolyze N-carbobenzoxy-glycyl-glycyl-L-arginine-B-napthylamide derivatives and to the use of an assay system which inhibits serum amino peptidase and enhances the detection of the *B. gingivalis* N-CBz-Gly-Gly-Arg peptidase. Serum enzymes, i.e. enzymes found in a natural environment, may be present in biological samples, for example, in gingival samples taken from infected areas, whether or not *B. gingivalis* was present. The present assay system was devised to inhibit the serum enzyme using a serum aminopeptidase inhibitor. As used herein, the term "serum aminopeptidase inhibitor" means any substance which inhibits the activity of serum aminopeptidase to a greater extent than it inhibits the activity of *B. gingivalis* N-CBz-Gly-Gly-Arg peptidase. Suitably, the present assay system also increases the reliability of detection of the *B. gingivalis* enzyme by enhancement of its specific enzyme activity. Substances useful in the present invention as enhancers, or enhancing materials, are chelating materials which enhance the enzyme activity of *B. gingivalis* N-CBz-Gly-Gly-Arg peptidase to a greater extent than such materials enhance the enzyme activity of serum aminopeptidase. Preferably, and for improved results, an inhibitor and an enhancing material are utilized in tandem. The determination is carried out on biological samples, such as subgingival plaque smears, by the formation of specific enzymes by *B. gingivalis*. The presence of such enzymes is subsequently determined, suitably, by colorimetric means. The biological samples may be cultured or in a natural environment. Such samples are typically fluid or in a fluid media. The enzyme assay, or analysis, techniques may include colorimetry, spectrophotometry, fluorospectrophotometry, gasometry, biochemical assays such as polyacrylamide gel eletrophoresis, immunologically using antibodies directed towards the enzyme or by antibodies directed towards related enzymes, or by DNA-DNA hybridization assays utilizing a DNA probe specific for the *B. gingivalis* gene coding for the N-CBz-glycyl-glycyl-arginylpeptidase. However, analysis is most suitably and simply carried out using a color determination wherein either the color of the substrate or the color of the end-product are utilized. Such determinations may be made manually, spectrophotometrically, densitometrically or fluorimetrically. The determination is based upon the unique properties of the *B. gingivalis* enzyme N-CBz-glycyl-glycyl-arginylpeptidase. The determination is suitably made by analysis of the activity of the above aylaminopeptidase.

The present assay system includes a serum amino peptidase inhibitor, for example, dimethyl-sulfoxide, (DMSO) and suitably includes a minor amount of an enhancing material, for example, a chelating material, such as tetrasodium ethylenediaminetetraacetate (EDTA).

The correlation between indirect immunofluorescent determination of B. gingivalis in subgingival plaque samples and the use of a colorimetric determination of arylaminopeptidase approaches r=0.5.

FIG. 1 is a comparison graph showing the relative effect of various inhibitors and enhancers on the B. gingivalis Tripeptidase. One unit of enzyme activity is defined as the amount of enzyme catalyzing the formation of one mM of β-naphthylamine at one hour at 37° C. The comparison tests shown in FIG. 1 were carried out using the following procedure: an assay system was prepared by mixing (a) 0.2 ml of 1 mM N-carbobenzoxy-glycyl-glycyl-L-arginine-β-naphthylamide hydrochloride with 0.6 ml of 0.1 M Tris-HCl, (b) the amount and type of inhibitor, enhancer or mixture thereof, as shown in FIG. 1, buffered at pH 7.0, and (c) 0.2 ml sample selected from either human serum, or B. gingivalis serum; the mixture was then incubated for one hour at 37° C.; subsequently 0.4 ml of a solution of stabilized diazonium salt, Fast Garnet GBC (0.5 mg/ml) in a 1M acetic acid buffer (pH 4.2), containing 10% Tween 20 was added; the mixture was allowed to stand for 15 minutes at room temperature, and; the color reaction read manually by comparison with the control solutions. The control solutions were run without enhancers or inhibitors.

DETAILED DESCRIPTION OF THE INVENTION

Figure 1:
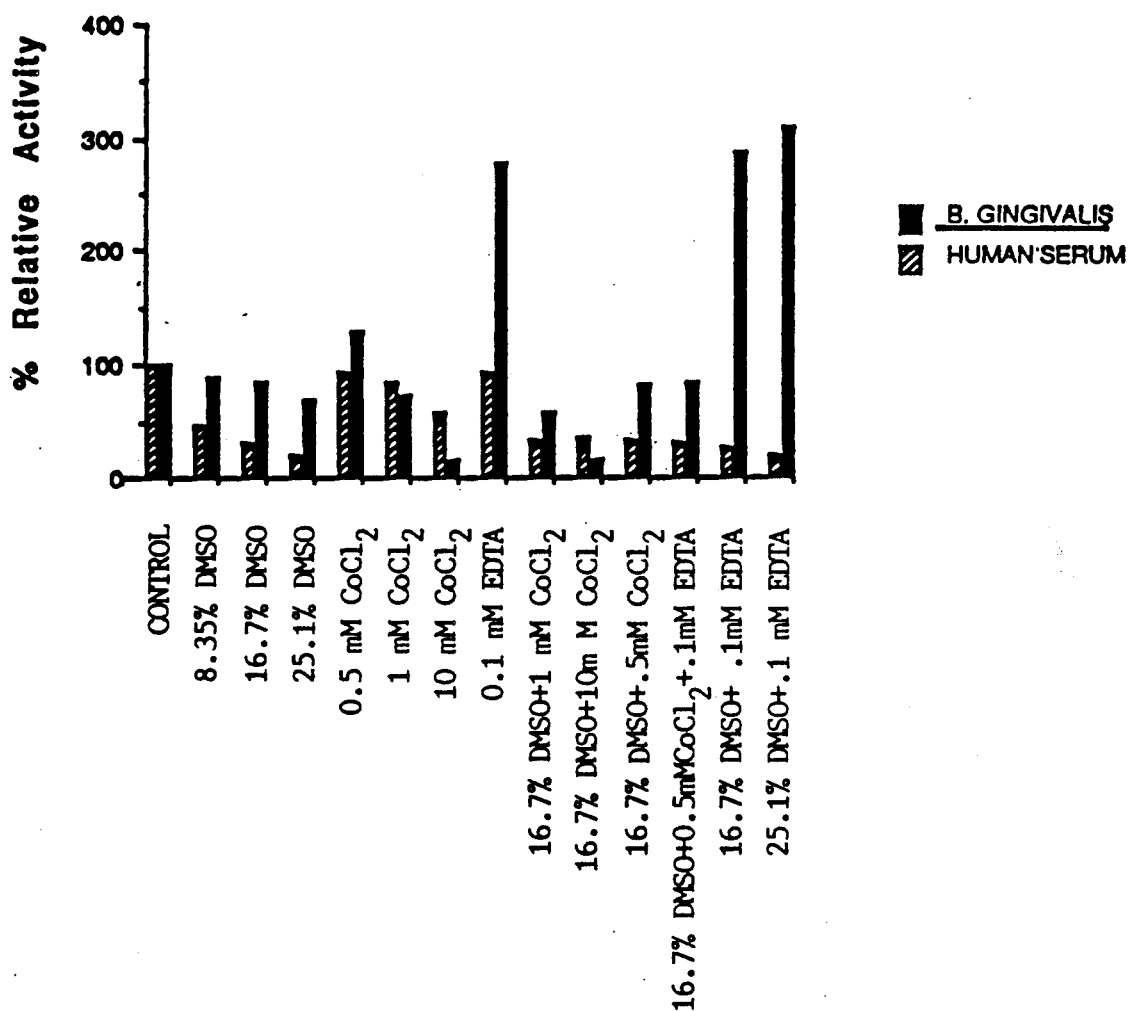

The present invention will now be described in greater detail in the following examples, which are not to be interpreted as limiting the invention.

EXAMPLE I

Table I shows the amylaminopeptiase activities of various black pigmented Bacteroides and Capnocytophage and illustrates the unique property of B. gingivalis to hydrolyze N-CBz-glycyl-glycyl-L-arginine-β-naphthylamide derivatives.

The enzyme activity was measured by the chromogenic properties of N-CBz-glycyl-glycyl-L-arginine-β-naphthylamide which upon hydrolysis gives a visible color. The aminopeptidase activities listed in the table reflect the nanomoles of β-naphthylamine liberated after 60 minutes under the conditions described below.

The assay system, or reaction mixture, was prepared by mixing 0.2 mL of 1 mM N-carbobenzoxy-glycyl-glycyl-L-arginine-β-naphthylamide hydrochloride with 0.6 ml of 0.1M Tris-HCl with 15 to 25% by volume DMSO and 0.1 mm EDTA buffered at pH 7.0 and 0.2 ml of plaque sample in phosphate buffered saline (pH 7.0). After mixing, the solution is incubated for 1 hour at 37° C. and then 0.4 ml of a solution of stabilized diazonium salt, Fast Garnet GBC (0.5 mg/ml) in a 1M acetic acid buffer (pH 4.2), containing 10% Tween 20 was added to the mixture. After standing for 15 minutes at room temperature, the color reaction can be read manually by comparison with standard solutions or the absorbancy can be determined using a spectrophotometer at 525 nm. The reaction mixture without enzyme solution is used as a control.

The assay systems useful in the present invention are those known and utilized in the art. Typical useful assay systems are described in Paunio et al, Acta Odontol Scand 29:583-590, 1971, and Umezawa et al, J. Antibot. 29:97-106, 1976. The present assay systems include a serum aminopepidase inhibitor, suitably a solvent, such as DMSO. Generally, amounts of between about 1 to about 50, and more preferably from about 5 to about 40 percent by volume, are found useful.

Suitably, the assay system includes a minor amount of a chelating agent to enhance the detection of B. gingivalis. Typically amounts between about 0.001 mM and about 10.0 mM, and more preferably between about 0.01 mM and about 1.0 mM are found useful. Generally, an amount of less than about 0.001 mM does not yield satisfactory enhancement and amounts greater than about 10.0 mM usually do not yield further worthwhile enhancement. Suitable chelating agents are bidentate or polydentate ligands, for example EDTA and N-hydroxyethylethylene-diaminetriacetic acid (HEDTA), their salts, typically sodium salts.

It will be noted from Table I that the black-pigmented Bacteroides species hydrolyzed few of the amino acid β-naphthylamides but strongly hydrolyzed most dipeptide substrates. B. gingivalis showed higher activities than did other Bacteroides against dipeptide derivatives including L-arginyl-L-arginine, glycyl-L-arginine-4-methoxy, and glycyl-L-proline-4-methoxy-β-naphthylamide. However, only B. gingivalis hydrolyzed N-CBz-glycyl-glycyl-L-arginine-β-naphthylamide derivatives. None of the other oral bacteria or Bacteroides species listed in Table I hydrolyzed the specific substrates to any significant degree.

Based on these data indicating that Bacteroides gingivalis produced a specific aminopeptidase, the N-CBz-glycyl-glycyl-arginylpeptidase, the specific activities of this enzyme were further examined. The peptidase activity of B. gingivalis to specifically produce N-CBz-glycyl-glycyl-arginylpeptidase was found to be cell associated and was not released into culture supernatants for up to 48 hours after sampling subgingival dental plaque. The enzyme activity was found to be optimal between pH 7.0 and 7.5 and readily inactivated by heat treatment by 45° C. for 15 minutes. The enzyme activity was found to be inhibited by DMSO p-chloromercuribenzoic acid, phenylmethylsulfonylfluoride, leupeptin and antipain indicating that it is a thiol protease. The B. gingivalis N-CBz-Gly-Gly-Arg peptidase was distinct from a serum enzyme which acts against a similar substrate. The serum enzyme was more resistant to heat treatment and is inhibited by diisopropylfluorophosphate. B. gingivalis enzyme activity was sensitive to heavy metal ions such as copper, mercury, and cadmium and was inhibited by high concentrations (>10 ml) of copper, zinc, mercury, cadmium, and cobalt.

It was found that using both an inhibitor, such as, DMSO, and an enhancer such as EDTA, that the B. gingivalis enzyme was enhanced over 300% and the serum enzyme activity was inhibited to about 75 to about 85% of its normal activity.

TABLE I

Aminopeptidase Activities of Black-Pigmented Bacteroides and Capnocytophaga

| Species Strains | Ala | Arg | α-Glu | His | Leu | Lys | D,L-Met | Pro | Arg-Arg | Gly-Arg | Gly-Phe | Gly-Pro | Leu-Gly | Lys-Ala | Lys-Pro | Ala-Ala-Phe | Gly-Pro-Leu | N-CBz-Gly-Gly-Arg |
|---|---|---|---|---|---|---|---|---|---|---|---|---|---|---|---|---|---|---|
| Bacteroides gingivalis | | | | | | | | | | | | | | | | | | |
| ATCC 33277 | 0 | 16 | 1 | 0 | 0 | 0 | 0 | 0 | 41 | 85 | 43 | 79 | 48 | 78 | 85 | 1 | 0 | 84 |
| 381 | 0 | 26 | 0 | 0 | 0 | 1 | 0 | 0 | 53 | 93 | 43 | 83 | 76 | 77 | 93 | 0 | 0 | 91 |
| 1021 | 0 | 15 | 0 | 0 | 0 | 2 | 0 | 0 | 22 | 69 | 12 | 41 | 16 | 50 | 68 | 0 | 0 | 44 |
| 11-1-2 | 0 | 9 | 0 | 0 | 0 | 0 | 0 | 0 | 70 | 94 | 40 | 85 | 47 | 63 | 85 | 0 | 2 | 92 |
| 9-14K-1 | 0 | 2 | 0 | 0 | 0 | 0 | 0 | 0 | 26 | 96 | 3 | 43 | 6 | 46 | 89 | 0 | 0 | 61 |
| FAYE 19m-1 | 0 | 3 | 0 | 0 | 0 | 1 | 0 | 0 | 32 | 234 | 14 | 49 | 6 | 43 | 152 | 3 | 0 | 143 |
| B. intermedius ATCC 25611 | 0 | 0 | 0 | 0 | 0 | 0 | 0 | 0 | 15 | 22 | 0 | 10 | 10 | 50 | 63 | 0 | 0 | 0 |
| B. mel. ss. intermedius | | | | | | | | | | | | | | | | | | |
| ATCC 25261 | 0 | 1 | 0 | 0 | 0 | 0 | 0 | 1 | 9 | 13 | 7 | 15 | 9 | 23 | 54 | 0 | 1 | 0 |
| ATCC 33563 | 0 | 1 | 0 | 0 | 0 | 0 | 0 | 0 | 21 | 9 | 0 | 22 | 2 | 17 | 75 | 0 | 2 | 1 |
| NCTC 9336 | 0 | 1 | 0 | 0 | 0 | 0 | 0 | 1 | 40 | 9 | 10 | 27 | 11 | 54 | 69 | 0 | 1 | 1 |
| B. asaccharolyticus | | | | | | | | | | | | | | | | | | |
| ATCC 18569 | 0 | 0 | 0 | 0 | 1 | 0 | 0 | 0 | 1 | 19 | 52 | 19 | 25 | 51 | 54 | 0 | 0 | 0 |
| ATCC 25260 | 0 | 3 | 0 | 0 | 1 | 1 | 1 | 2 | 10 | 11 | 18 | 41 | 37 | 34 | 41 | 0 | 3 | 0 |
| ATCC 27067 | 0 | 2 | 0 | 1 | 0 | 3 | 2 | 2 | 15 | 27 | 44 | 52 | 51 | 48 | 54 | 0 | 4 | 0 |
| 536B | 0 | 3 | 0 | 0 | 0 | 2 | 0 | 1 | 15 | 16 | 18 | 70 | 49 | 76 | 85 | 0 | 3 | 1 |
| NY446 | 1 | 0 | 0 | 0 | 0 | 0 | 0 | 0 | 4 | 5 | 0 | 18 | 0 | 38 | 62 | 0 | 0 | 2 |
| B. corporis ATCC 33547 | 0 | 1 | 0 | 0 | 0 | 0 | 0 | 0 | 4 | 0 | 43 | 54 | 67 | 68 | 75 | 0 | 2 | 1 |
| B. melaninogenicus ATCC 25845 | 1 | 1 | 1 | 0 | 1 | 2 | 1 | 2 | 24 | 4 | 40 | 26 | 53 | 78 | 70 | 1 | 2 | 0 |
| B. denticola ATCC 33185 | 1 | 1 | 0 | 1 | 1 | 1 | 0 | 1 | 16 | 4 | 2 | 17 | 42 | 89 | 86 | 2 | 1 | 0 |
| B. loescheii | | | | | | | | | | | | | | | | | | |
| ATCC 15930 | 1 | 1 | 0 | 1 | 0 | 1 | 0 | 0 | 5 | 11 | 55 | 82 | 20 | 42 | 81 | 1 | 1 | 1 |
| VPI4196 | 1 | 3 | 0 | 0 | 1 | 0 | 0 | 1 | 13 | 3 | 40 | 39 | 58 | 86 | 89 | 0 | 1 | 0 |
| B. levii | | | | | | | | | | | | | | | | | | |
| 18-1-5 | 0 | 1 | 0 | 0 | 0 | 0 | 0 | 1 | 2 | 0 | 48 | 22 | 47 | 45 | 51 | 0 | 1 | 0 |
| 18-1-8 | 0 | 0 | 2 | 0 | 0 | 0 | 1 | 0 | 0 | 1 | 51 | 17 | 51 | 48 | 54 | 0 | 0 | 1 |
| Capnocytophaga gingivalis ATCC 33624 | 139 | 221 | 5 | 10 | 203 | 211 | 122 | 1 | 65 | 6 | 33 | 19 | 8 | 54 | 176 | 72 | 58 | 7 |
| C. ochracea ATCC 27872 | 136 | 160 | 5 | 14 | 157 | 157 | 118 | 0 | 71 | 11 | 36 | 11 | 9 | 50 | 108 | 82 | 41 | 8 |
| C. sputigena ATCC 33123 | 145 | 148 | 7 | 9 | 158 | 139 | 117 | 0 | 18 | 8 | 47 | 16 | 20 | 36 | 86 | 44 | 28 | 5 |
| Capnocytophaga sp. JD3-5 | 19 | 67 | 0 | 0 | 37 | 62 | 28 | 0 | 0 | 20 | 0 | 2 | 0 | 14 | 35 | 0 | 0 | 0 |

The following is a key to the β-naphthylamide substrate abbreviations used in the tables:

| | |
|---|---|
| Ala = | Alanine |
| Arg = | Arginine |
| α-Glu = | α-glutamine |
| His = | Histidine |
| Leu = | iso-leucine |
| Lys = | lysine |
| D, L-Met = | D, L Methionine |
| Pro = | Proline |
| Arg—Arg = | Arginyl-arginine |
| Gly—Arg = | Glycyl-arginine |
| Gly—Phe = | Glycyl-phenylalanine |
| Gly—Pro = | Glycyl-proline |
| Leu—Gly = | Leucyl-glycine |
| Lys—Ala = | Lysyl-alanine |
| Lys-Pro = | Lysyl-proline |
| Ala—Ala—Phe = | Alanyl-alanyl-phenylalanine |
| Gly—Pro—Leu = | Glycyl-prolyl-leucine |
| N—CBz—Gly—Gly—Arg = | N-CBz-glycyl-glycyl-arginine |

Table II shows the aminopeptidase activity of Actinobacillus, Haemophilus, and other bacterial species. Table III illustrates similar activity of Actinomyces, Streptococcus, and Lactobacillus. The enzyme activity and the aminopeptidase activities were determined in the manner described above in regard to Table I.

TABLE II

Aminopeptidase Activities of Actinobacillus, Haemophilus and other bacteria.

| Species Strains | Ala | Arg | α-Glu | His | Leu | Lys | D,L-Met | Pro | Arg-Arg | Gly-Arg | Gly-Phe | Gly-Pro | Leu-Gly | Lys-Ala | Lys-Pro | Ala-Ala-Phe | Gly-Pro-Leu | N-CBz-Gly-Gly-Arg |
|---|---|---|---|---|---|---|---|---|---|---|---|---|---|---|---|---|---|---|
| *Actinobacillus actinomycetemcomitans* | | | | | | | | | | | | | | | | | | |
| NCTC 9709 | 0 | 0 | 0 | 0 | 1 | 0 | 0 | 0 | 2 | 0 | 0 | 0 | 0 | 0 | 0 | 1 | 0 | 1 |
| ATCC 29523 | 1 | 1 | 0 | 0 | 3 | 5 | 1 | 0 | 0 | 1 | 0 | 1 | 0 | 0 | 0 | 0 | 0 | 0 |
| Y4 | 1 | 1 | 0 | 0 | 1 | 1 | 0 | 0 | 0 | 0 | 0 | 0 | 0 | 1 | 1 | 0 | 0 | 0 |
| 67 | 3 | 7 | 0 | 2 | 6 | 5 | 0 | 0 | 2 | 4 | 0 | 5 | 2 | 1 | 1 | 3 | 1 | 0 |
| 75 | 0 | 2 | 0 | 0 | 0 | 1 | 0 | 0 | 3 | 1 | 0 | 4 | 0 | 0 | 2 | 1 | 1 | 0 |
| *A. equuli* ATCC 19392 | 0 | 1 | 0 | 0 | 0 | 1 | 0 | 1 | 0 | 0 | 0 | 0 | 0 | 0 | 0 | 0 | 0 | 0 |
| *A. seminis* ATCC 15768 | 0 | 2 | 0 | 0 | 0 | 0 | 0 | 0 | 0 | 0 | 0 | 0 | 0 | 0 | 0 | 0 | 0 | 1 |
| *A. suis* ATCC 15557 | 0 | 0 | 0 | 0 | 0 | 0 | 0 | 0 | 0 | 0 | 0 | 0 | 0 | 0 | 0 | 0 | 0 | 0 |
| *Haemophilus aphrophilus* | | | | | | | | | | | | | | | | | | |
| NCTC 5908 | 1 | 0 | 0 | 0 | 0 | 3 | 0 | 0 | 0 | 0 | 0 | 0 | 0 | 0 | 0 | 0 | 0 | 0 |
| ATCC 13252 | 0 | 1 | 0 | 0 | 0 | 2 | 0 | 1 | 1 | 0 | 0 | 1 | 0 | 0 | 0 | 0 | 0 | 1 |
| ATCC 19415 | 0 | 1 | 0 | 0 | 0 | 0 | 0 | 1 | 1 | 0 | 0 | 0 | 0 | 0 | 0 | 0 | 0 | 1 |
| *Campylobacter sputorum* Ba1-21 | 3 | 0 | 1 | 0 | 0 | 3 | 0 | 2 | 1 | 0 | 0 | 1 | 0 | 0 | 3 | 0 | 2 | 0 |
| *Eikenella corrodens* BP1-6 | 1 | 0 | 0 | 0 | 0 | 0 | 3 | 194 | 0 | 2 | 0 | 0 | 0 | 0 | 0 | 0 | 0 | 0 |
| *Fusobacterium nucleatum* | | | | | | | | | | | | | | | | | | |
| ATCC 25586 | 0 | 0 | 0 | 0 | 0 | 0 | 0 | 0 | 1 | 0 | 0* | 0 | 0 | 0 | 2 | 3 | 2 | 0 |
| D31A-24 | 0 | 2 | 1 | 0 | 0 | 0 | 0 | 1 | 2 | 1 | 0 | 0 | 0 | 0 | 2 | 0 | 2 | 2 |
| 2 | 2 | 0 | 0 | 2 | 2 | 0 | 1 | 2 | 1 | 0 | 2 | 0 | 2 | 2 | 1 | 2 | 0 | 3 |
| *F. periodonticum* EK1-15 | 0 | 0 | 0 | 0 | 1 | 1 | 0 | 0 | 1 | 0 | 0 | 1 | 0 | 0 | 1 | 1 | 1 | 0 |
| *Veillonella alcalesens* ATCC 11748 | 3 | 1 | 0 | 0 | 2 | 0 | 0 | 10 | 0 | 0 | 0 | 0 | 0 | 0 | 1 | 1 | 0 | 0 |
| *V. parvula* ATCC 10790 | 2 | 0 | 0 | 0 | 0 | 0 | 0 | 7 | 0 | 0 | 0 | 0 | 0 | 0 | 0 | 0 | 0 | 0 |
| *Veillonella* sp. SE1M2 | 0 | 0 | 0 | 0 | 0 | 0 | 0 | 1 | 0 | 0 | 0 | 0 | 0 | 0 | 1 | 0 | 0 | 0 |
| "Anaerobic vibrio" SN2T2 | 1 | 0 | 0 | 0 | 3 | 0 | 0 | 0 | 0 | 0 | 0 | 0 | 0 | 0 | 3 | 0 | 0 | 1 |

TABLE III

Aminopeptidase Activities of Actinomyces, Streptococcus and Lactobacillus.

| Species Strains | Ala | Arg | α-Glu | His | Leu | Lys | D,L-Met | Pro | Arg-Arg | Gly-Arg | Gly-Phe | Gly-Pro | Leu-Gly | Lys-Ala | Lys-Pro | Ala-Ala-Phe | Gly-Pro-Leu | N-CBz-Gly-Gly-Arg |
|---|---|---|---|---|---|---|---|---|---|---|---|---|---|---|---|---|---|---|
| *Actinomyces israeli* | | | | | | | | | | | | | | | | | | |
| ATCC 12103 | 7 | 0 | 0 | 0 | 28 | 2 | 12 | 15 | 0 | 0 | 0 | 0 | 0 | 0 | 1 | 3 | 0 | 0 |
| DK2-3 | 5 | 0 | 0 | 2 | 84 | 1 | 33 | 12 | 0 | 0 | 0 | 0 | 0 | 0 | 0 | 0 | 0 | 0 |
| *A. viscosus* | | | | | | | | | | | | | | | | | | |
| ATCC 19246 | 0 | 0 | 0 | 0 | 21 | 0 | 9 | 29 | 0 | 0 | 0 | 0 | 0 | 0 | 5 | 2 | 0 | 0 |
| T14V | 1 | 1 | 0 | 0 | 17 | 3 | 7 | 31 | 0 | 2 | 0 | 0 | 0 | 0 | 7 | 4 | 2 | 0 |
| *Streptococcus mitis* | | | | | | | | | | | | | | | | | | |
| ATCC 9815 | 14 | 105 | 0 | 0 | 91 | 76 | 52 | 0 | 43 | 1 | 1 | 120 | 0 | 15 | ND[b] | 3 | 27 | 0 |
| ATCC 15909 | 9 | 5 | 0 | 0 | 32 | 21 | 12 | 0 | 2 | 2 | 0 | 114 | 0 | 1 | 8 | 1 | 7 | 0 |
| ATCC 15911 | 5 | 154 | 0 | 1 | 25 | 23 | 13 | 0 | 18 | 4 | 0 | 328 | 124 | 0 | 7 | 0 | | |
| ATCC 15912 | 5 | 153 | 0 | 0 | 36 | 36 | 17 | 0 | 24 | 59 | 0 | 169 | 0 | 21 | 141 | 0 | 11 | 0 |
| *S. mutans* ATCC 25175 | 1 | 1 | 0 | 0 | 10 | 10 | 5 | 0 | 1 | 0 | 0 | 22 | 0 | 2 | 14 | 0 | 0 | 0 |
| *S. salivarius* | | | | | | | | | | | | | | | | | | |
| ATCC 9759 | 3 | 48 | 0 | 0 | 14 | 9 | 5 | 0 | 24 | 0 | 0 | 105 | 0 | 4 | 6 | 0 | 2 | 0 |
| ATCC 25975 | 0 | 43 | 0 | 0 | 4 | 5 | 1 | 0 | 15 | 0 | 0 | 90 | 0 | 17 | 33 | 0 | 0 | 0 |

TABLE III-continued

Aminopeptidase Activities of Actinomyces, Streptococcus and Lactobacillus.

| Species Strains | Ala | Arg | a-Glu | His | Leu | Lys | D,L-Met | Pro | Arg-Arg | Gly-Arg | Gly-Phe | Gly-Pro | Leu-Gly | Lys-Ala | Lys-Pro | Ala-Ala-Phe | Gly-Pro-Leu | N-CBz-Gly-Gly-Arg |
|---|---|---|---|---|---|---|---|---|---|---|---|---|---|---|---|---|---|---|
| *S. sanguis* | | | | | | | | | | | | | | | | | | |
| ATCC 10556 | 16 | 17 | 0 | 1 | 49 | 20 | 23 | 0 | 2 | 3 | 1 | 75 | 0 | 1 | 5 | 2 | 11 | 0 |
| ATCC 10557 | 13 | 6 | 0 | 0 | 49 | 19 | 18 | 0 | 0 | 3 | 0 | 109 | 0 | 0 | 4 | 1 | 6 | 0 |
| *Lactobacillus casei* | | | | | | | | | | | | | | | | | | |
| ATCC 11578 | 10 | 0 | 3 | 8 | 33 | 4 | 9 | 1 | 1 | 0 | 2 | 9 | 2 | 0 | 0 | 3 | 0 | 0 |
| ATCC 11582 | 11 | 0 | 3 | 7 | 37 | 1 | 9 | 2 | 0 | 1 | 2 | 8 | 1 | 0 | 0 | 3 | 0 | 0 |
| ATCC 7469 | 2 | 0 | 0 | 0 | 5 | 0 | 1 | 0 | 1 | 0 | 0 | 1 | 0 | 0 | 0 | 0 | 0 | 0 |
| *L. fermentum* ATCC 11581 | 7 | 0 | 0 | 3 | 22 | 0 | 6 | 0 | 0 | 0 | 2 | 5 | 2 | 2 | 0 | 5 | 0 | 0 |

*ND: not determined.*

EXAMPLE II

A clinical study was performed to examine the correlation between the detection of *Bacteroides gingivalis* from subgingival dental plaque by indirect immunofluorescence microscopy and the detection of the organism by colorimetric assay of the arylaminopeptidase activities.

Ten male and female subjects between 52–76 years of age were selected from untreated periodontitis patients in the Periodontics Clinic of the State University of Buffalo School of Dental Medicine. From each patient, subgingival plaque and gingival crevicular fluid samples were obtained, clinical indices were recorded at each site including the Plaque Index of Silness and Löe, the Gingival Index of Löe and Silness, and probing pocket depth measurement using a Michigan O Probe. The teeth were isolated with cotton rolls and the subgingival plaque was removed using sterile cotton pellets. Subgingival plaque samples were obtained by inserting 5 sterile fine paper points to the depth of the periodontal pocket for 10 seconds and then immediately placing the samples into tubes containing 1.5 ml of 0.01M phosphate buffered saline, pH 7.0. The samples were used as gingival crevicular fluid samples for microbial analysis and for determination of enzyme activities.

Within one hour of collection the plaque samples were dispersed using a vortex mixer for 1 min. at maximal setting in order to separate microorganisms from the paper points. The dispersed plaque samples were examined in a Petroff-Hausser counting chamber using dark field microscopy at a magnification of 1000×. The plaque microorganisms were classified as cocci rods, filaments, fusiforms, motile rods, and small, medium, and large spirochetes. 10 ul aliquots of undiluted plaque suspensions were distributed onto glass slides, gently heat-fixed, and stored at room temperature. Smears were stained within one week of sampling with 10 ul of rabbit antisera to *B. gingivalis* diluted to appropriate working titer in phosphate buffer saline, pH 7.2. Slides were incubated in a humid chamber at 37° C. for 30 min., rinsed with phosphate buffered saline (PBS) containing 0.05% Tween 20, washed in a PBS-Tween 20 mixture for 10 min., and rinsed with distilled water. The smears were then incubated for 45 min. with 10 ul of goat anti rabbit IgG conjugated with fluorescein isothiocyanate diluted in PBS-Tween 20 to working titer. Slides were rinsed and washed as before and then mounted with glycerol in PBS, pH 9.0. The stained bacterial smears were examined with a Leitz orthoplan microscope equipped for phase contrast and for incident light fluorescence. The light source was Osram HBO-200 mercury lamp with a BG12 filter and dichroic 495 nm interference filter and a K510 suppression filter. Fluorescence intensity was graded from 0-4+ with significant immunological reactions corresponding to grades 3+ and 4+ revealing yellow-green fluorescence with a clear cell outline and a sharply defined, nonstaining center of the cell. Between 100–200 bacterial cells were counted and the number of fluorescence cells as a proportion of the total cell count ascertained by phase contrast microscopy was determined for each sample.

Arylaminopeptidase activities in gingival crevicular fluid samples were measured. The substrates used in this study included N-carbobenzoxy-glycyl-glycyl-L-arginine-β-naphthylamide hydrochloride.

The relation of subgingival plaque bacteria to arylaminopeptidase activities in gingival crevicular fluid samples was examined by calculation of correlation coefficients between the percent of specific subgingival plaque microorganisms and N-CBz-gly-gly-L-arg-β-naphthylamide peptidase activity in gingival crevicular fluid samples. There is a 0.42 correlation between the number of subgingival *B. gingivalis* and cleavage of the specific substrate indicating the usefulness of assays for this enzymatic activity in determining the number of subgingival *Bacteroides gingivalis*. There was also a significant difference ($P<0.05$) between levels of N-CBz-gly-gly-arg peptidase activity and sites exhibiting probing pocket depths of 4 mm as compared to probing pocket depth of 5 mm as well as between sites exhibiting gingival indices of 2 compared to sites with gingival indices of 3.

Modifications of the present invention will be apparent to those skilled in the art. It is, therefore, intended that the present invention be limited only by the scope of the following claims.

What is claimed is:

1. A method for the detection of *B. gingivalis* in a biological sample which comprises the steps of:
   (a) mixing said sample with N-CBz-glycyl-glycyl-L-arginine-β-naphthylamide or a derivative thereof,
   (b) adding a dimethyl sulfoxide serum aminopeptidase inhibitor, and
   (c) detecting the amount of *B. gingivalis* N-CBz-Gly-Gly-Arg peptidase in said sample.

2. The method of claim 1 wherein the amount of dimethyl sulfoxide ranges between about 1 and about 50 percent by volume.

3. The method of claim 1 wherein a chelating material is added in an amount sufficient to enhance the detection of *B. gingivalis* N-C-Bz-Gly-Gly-Arg peptidase.

4. The method of claim 4 wherein the chelating material is a bidentate or polydentate ligand.

5. The method of claim 5 wherein the chelating material is selected from the group consisting of tetrasodium ethylenediaminetetracetate, N-hydroxethylethylenediaminetriacetic acid, their salts, and mixtures thereof.

* * * * *

UNITED STATES PATENT AND TRADEMARK OFFICE
CERTIFICATE OF CORRECTION

PATENT NO. : 4,994,376

DATED : February 19, 1991

INVENTOR(S) : Joseph J. Zambon & Robert J. Genco

It is certified that error appears in the above-identified patent and that said Letters Patent is hereby corrected as shown below:

Column 12, line 1:
Claim 4 should be dependent from Claim 3 rather than from Claim 4.

Column 13, line 3:
Claim 5 should be dependent from Claim 4 rather than from Claim 5.

On the title page, in item [75]:
The inventor's name on page 1 should read Robert J. Genco rather than Robert J. Gence.

Signed and Sealed this

Twentieth Day of October, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,994,376
DATED : Feb. 19, 1991
INVENTOR(S) : Joseph J. Zambon et al.

It is certified that error appears in the above—identified patent and that said Letters Patent is hereby corrected as shown below:

In Columns 7 and 8, Table III, entries for the species strain ATCC 15911 should appear as follows:

5  154  0  1  25  23  13  0  18  4  0  328  0  23  124  0  7  0

Signed and Sealed this

Third Day of August, 1993

Attest:

MICHAEL K. KIRK

*Attesting Officer*   Acting Commissioner of Patents and Trademarks